(12) United States Patent
Tanner et al.

(10) Patent No.: US 8,749,790 B1
(45) Date of Patent: Jun. 10, 2014

(54) STRUCTURE AND METHOD TO MEASURE WAVEGUIDE POWER ABSORPTION BY SURFACE PLASMON ELEMENT

(75) Inventors: Shawn M. Tanner, San Jose, CA (US); Yufeng Hu, Fremont, CA (US); Ut Tran, San Jose, CA (US); Zhongyan Wang, San Ramon, CA (US); Zhong Shi, Dublin, CA (US); Sergei Sochava, Sunnyvale, CA (US)

(73) Assignee: Western Digital (Fremont), LLC, Fremont, CA (US)

( * ) Notice: Subject to any disclaimer, the term of this patent is extended or adjusted under 35 U.S.C. 154(b) by 216 days.

(21) Appl. No.: 13/314,962

(22) Filed: Dec. 8, 2011

(51) Int. Cl.
*G01N 21/55* (2006.01)

(52) U.S. Cl.
USPC ............ 356/445; 356/446; 369/13.33; 385/6; 385/14; 359/245; 359/247

(58) Field of Classification Search
CPC .... G01N 21/554; G01N 21/474; G01N 21/57
USPC ............ 356/445–446; 385/6, 14, 37; 359/245
See application file for complete search history.

(56) References Cited

U.S. PATENT DOCUMENTS

| | | |
|---|---|---|
| 4,670,732 A | 6/1987 | Church |
| 4,675,986 A | 6/1987 | Yen |
| 5,065,483 A | 11/1991 | Zammit |
| 5,199,090 A | 3/1993 | Bell |
| 5,210,667 A | 5/1993 | Zammit |
| 5,463,805 A | 11/1995 | Mowry et al. |
| 5,559,429 A | 9/1996 | Mowry et al. |
| 5,597,340 A | 1/1997 | Church et al. |
| 5,722,155 A | 3/1998 | Stover et al. |
| 5,755,612 A | 5/1998 | Schaenzer et al. |
| 5,816,890 A | 10/1998 | Hao et al. |
| 5,876,264 A | 3/1999 | Church et al. |
| 6,027,397 A | 2/2000 | Church et al. |
| 6,034,849 A | 3/2000 | Takizawa |
| 6,047,224 A | 4/2000 | Stover et al. |
| 6,193,584 B1 | 2/2001 | Rudy et al. |
| 6,256,170 B1 | 7/2001 | Honda |

(Continued)

OTHER PUBLICATIONS

Ikkawi, R.; Amos, N.; Lavrenov, A.; Krichevsky, A.; Teweldebrhan,D.; Ghosh, S.; Balandin, A.A.; Litinov, D.; & Khizroev; Near-Field Optical Transducer for Heat-Assisted Magnetic Recording for Beyond-10-Tbit/in2 Densities, Journal of Nanoelectronics and Optoelectronis, vol. 3, 44-54, 2008.

(Continued)

*Primary Examiner* — Tarifur Chowdhury
*Assistant Examiner* — Isiaka Akanbi

(57) ABSTRACT

A structure for measuring energy absorption by a surface plasmon receptor or NFT on a waveguide comprises a first waveguide, a first input grating for coupling light comprising a first wavelength into the first waveguide, a first output grating for coupling light out of the first waveguide, a first plurality of surface plasmon receptors in cooperation with the first waveguide to receive light energy and located between the first input grating and the first output grating. The structure may further comprise a second waveguide, a second input grating for coupling light into the second waveguide, a second output grating for coupling light out of the second waveguide, a second plurality of surface plasmon receptors between the second input grating and the second output grating and in cooperation with the second waveguide to receive light energy, wherein the second plurality may be less than or greater than the first plurality.

14 Claims, 7 Drawing Sheets

(56) References Cited

U.S. PATENT DOCUMENTS

| | | |
|---|---|---|
| 6,330,488 B1 | 12/2001 | Yoshida et al. |
| 6,347,983 B1 | 2/2002 | Hao et al. |
| 6,399,401 B1 | 6/2002 | Kye et al. |
| 6,532,646 B2 | 3/2003 | Watanuki |
| 6,609,948 B1 | 8/2003 | Fontana, Jr. et al. |
| 6,623,330 B2 | 9/2003 | Fukuroi |
| 6,684,171 B2 | 1/2004 | Church et al. |
| 6,699,102 B2 | 3/2004 | Reiley et al. |
| 6,728,067 B2 | 4/2004 | Crawforth et al. |
| 6,758,722 B2 | 7/2004 | Zhu |
| 6,795,630 B2 | 9/2004 | Challener et al. |
| 6,834,027 B1 | 12/2004 | Sakaguchi et al. |
| 6,857,937 B2 | 2/2005 | Bajorek |
| 6,884,148 B1 | 4/2005 | Dovek et al. |
| 6,950,289 B2 | 9/2005 | Lam et al. |
| 6,982,042 B2 | 1/2006 | Church et al. |
| 7,014,530 B2 | 3/2006 | Kasiraj et al. |
| 7,034,277 B2 | 4/2006 | Oumi et al. |
| 7,139,152 B2 | 11/2006 | Mahnad et al. |
| 7,149,061 B2 | 12/2006 | Yamakura et al. |
| 7,186,348 B2 | 3/2007 | Chen et al. |
| 7,206,172 B2 | 4/2007 | Ding et al. |
| 7,215,629 B2 | 5/2007 | Eppler |
| 7,244,169 B2 | 7/2007 | Cyrille et al. |
| 7,245,459 B2 | 7/2007 | Cyrille et al. |
| 7,268,976 B2 | 9/2007 | Yamakura et al. |
| 7,271,982 B2 | 9/2007 | MacDonald et al. |
| 7,272,079 B2 | 9/2007 | Challener |
| 7,272,883 B2 | 9/2007 | Le et al. |
| 7,287,316 B2 | 10/2007 | Kasahara et al. |
| 7,330,404 B2 | 2/2008 | Peng et al. |
| 7,333,300 B2 | 2/2008 | Church et al. |
| 7,359,152 B2 | 4/2008 | Matono et al. |
| 7,360,296 B2 | 4/2008 | Cyrille et al. |
| 7,393,262 B2 | 7/2008 | Biskeborn |
| 7,480,214 B2 | 1/2009 | Challener et al. |
| 7,642,205 B2 | 1/2010 | Timans |
| 7,710,686 B2 | 5/2010 | Kim et al. |
| 7,724,470 B2 | 5/2010 | Poon et al. |
| 7,821,732 B2 | 10/2010 | Komura et al. |
| 7,861,400 B2 | 1/2011 | Lille |
| 7,936,531 B2 | 5/2011 | Tomikawa et al. |
| 7,948,714 B2 | 5/2011 | Yin et al. |
| 7,996,986 B2 | 8/2011 | Gokemeijer |
| 8,077,418 B1 | 12/2011 | Hu et al. |
| 8,085,459 B1 * | 12/2011 | Russell et al. ............... 359/245 |
| 8,111,443 B1 * | 2/2012 | Russell et al. ............... 359/245 |
| 8,179,628 B2 | 5/2012 | Zhou et al. |
| 8,200,054 B1 * | 6/2012 | Li et al. ...................... 385/37 |
| 8,248,891 B2 | 8/2012 | Lee et al. |
| 8,248,896 B1 | 8/2012 | Yuan et al. |
| 8,302,480 B2 | 11/2012 | Maris et al. |
| 8,325,566 B2 | 12/2012 | Shimazawa et al. |
| 8,339,905 B2 | 12/2012 | Rausch et al. |
| 8,343,364 B1 | 1/2013 | Gao et al. |
| 8,375,565 B2 | 2/2013 | Hu et al. |
| 8,411,393 B2 | 4/2013 | Zou et al. |
| 8,486,286 B1 | 7/2013 | Gao et al. |
| 2002/0044285 A1 * | 4/2002 | Pedersen et al. ............ 356/445 |
| 2003/0020467 A1 | 1/2003 | Kasahara et al. |
| 2003/0112542 A1 | 6/2003 | Rettner et al. |
| 2003/0128634 A1 | 7/2003 | Challener |
| 2003/0137772 A1 | 7/2003 | Challener |
| 2003/0184903 A1 | 10/2003 | Challener |
| 2004/0001394 A1 | 1/2004 | Challener et al. |
| 2004/0110365 A1 | 6/2004 | Su et al. |
| 2004/0179310 A1 | 9/2004 | Lam et al. |
| 2005/0023673 A1 | 2/2005 | Nowak |
| 2005/0052771 A1 | 3/2005 | Rausch et al. |
| 2005/0067372 A1 | 3/2005 | Li et al. |
| 2005/0067374 A1 | 3/2005 | Baer et al. |
| 2005/0078565 A1 | 4/2005 | Peng et al. |
| 2005/0122850 A1 | 6/2005 | Challener et al. |
| 2006/0000795 A1 | 1/2006 | Chen et al. |
| 2006/0028770 A1 | 2/2006 | Etoh et al. |
| 2006/0044683 A1 | 3/2006 | Matono et al. |
| 2006/0103990 A1 | 5/2006 | Ito et al. |
| 2006/0126222 A1 | 6/2006 | Aoki et al. |
| 2006/0233061 A1 | 10/2006 | Rausch et al. |
| 2007/0008660 A1 | 1/2007 | Yamakura et al. |
| 2007/0116420 A1 * | 5/2007 | Estes et al. .................. 385/130 |
| 2007/0139816 A1 | 6/2007 | Chen et al. |
| 2007/0159720 A1 | 7/2007 | Sohn et al. |
| 2007/0165495 A1 * | 7/2007 | Lee et al. .................. 369/13.33 |
| 2007/0177300 A1 | 8/2007 | Yin et al. |
| 2008/0005543 A1 | 1/2008 | Rychlik |
| 2008/0068748 A1 | 3/2008 | Olson et al. |
| 2008/0072418 A1 | 3/2008 | Kondo et al. |
| 2008/0144215 A1 | 6/2008 | Hsiao et al. |
| 2008/0158730 A1 | 7/2008 | Furukawa et al. |
| 2008/0181560 A1 | 7/2008 | Suh et al. |
| 2008/0204916 A1 | 8/2008 | Matsumoto et al. |
| 2008/0232225 A1 | 9/2008 | Cho et al. |
| 2009/0165285 A1 | 7/2009 | Takayama et al. |
| 2009/0185459 A1 | 7/2009 | Matsumoto |
| 2010/0118664 A1 | 5/2010 | Nishida et al. |
| 2010/0123900 A1 * | 5/2010 | Chau et al. .................. 356/445 |
| 2010/0142079 A1 | 6/2010 | Tanaka et al. |
| 2010/0157745 A1 | 6/2010 | Okada et al. |
| 2010/0208391 A1 | 8/2010 | Gokemeijer |
| 2010/0214685 A1 | 8/2010 | Seigler et al. |
| 2010/0315735 A1 | 12/2010 | Zhou et al. |
| 2010/0316327 A1 * | 12/2010 | Montoya et al. .................. 385/6 |
| 2010/0321814 A1 | 12/2010 | Zou et al. |
| 2011/0122737 A1 | 5/2011 | Shimazawa et al. |
| 2011/0179634 A1 | 7/2011 | Yin et al. |
| 2011/0216635 A1 | 9/2011 | Matsumoto |
| 2011/0235480 A1 | 9/2011 | Goulakov et al. |
| 2011/0292774 A1 | 12/2011 | Osawa et al. |
| 2011/0294398 A1 | 12/2011 | Hu et al. |
| 2012/0092971 A1 | 4/2012 | Schreck et al. |
| 2012/0155232 A1 | 6/2012 | Schreck et al. |
| 2012/0163137 A1 | 6/2012 | Wang et al. |
| 2012/0230138 A1 | 9/2012 | Endo |

OTHER PUBLICATIONS

Chubing Peng, "Surface-plasmon resonance of a planar lollipop near-field transducer", Applied Physics Letters 94, 171106-1, Apr. 2009, 4 pages.

Bill Challenger, "Plasmonic transducer for near field heat assisted magnetic recording", 2009 CMOS Emerging Technologies Workshop, Sep. 24, 2009, 19 pages.

* cited by examiner

| m | N=2 | N=3 | N=4 | N=5 | N=6 | N=7 | N=8 |
|---|---|---|---|---|---|---|---|
| 1 | 4 | 4 | 4 | 4 | 4 | 4 | 4 |
| 2 | | 4.115 | 4.077 | 4.058 | 4.046 | 4.038 | 4.033 |
| 3 | | | 4.154 | 4.115 | 4.092 | 4.077 | 4.066 |
| 4 | | | | 4.173 | 4.138 | 4.115 | 4.099 |
| 5 | | | | | 4.184 | 4.154 | 4.132 |
| 6 | | | | | | 4.192 | 4.165 |

$D_0 = 4$ μm
$\lambda = 0.83$ μm
$n = 1.8$

FIG. 11

STRUCTURE AND METHOD TO MEASURE WAVEGUIDE POWER ABSORPTION BY SURFACE PLASMON ELEMENT

BACKGROUND OF THE INVENTION

To increase the areal storage density of a magnetic recording device, the recording layer thereof may be provided with smaller and smaller individual magnetic grains. This reduction in grain size soon reaches a limit at which point the magnetic grains become thermally unstable and incapable of maintaining their magnetization. The thermal stability of the magnetic grains can be increased by increasing the magnetic anisotropy thereof (e.g., by utilizing materials with higher anisotropic constants). Increasing the magnetic anisotropy of the magnetic grains, however, increases their coercivity and therefore requires a stronger magnetic field to change the magnetic orientation of the grains (e.g., in a write operation).

Energy-assisted magnetic recording (EAMR) may be used to address this challenge. In an EAMR system, a small spot where data is to be written is locally heated to reduce the coercivity of the magnetic grains therein for the duration of the write operation, thereby allowing materials with increased magnetic anisotropy to be used, and greater areal storage density to be exploited.

In one EAMR approach, a semiconductor laser diode may be used as a light source and coupled to a planar waveguide which serves as light delivery path. A grating structure may be used to couple the laser light into the waveguide. The coupled light is then routed to a near field transducer (NFT) by which the optical energy is provided to a small optical spot on the recording media a few tens of nanometers (nm) in size.

NFT's are typically mounted on a waveguide to take advantage the surface plasmon waves to create local electromagnetic fields. Light from the waveguide impinges on the NFT and causes a surface charge that can be transferred to an antenna portion of the NFT; and becomes useful for transferring energy from the antenna to a receptor such as recording media. NFT designs and antenna shapes vary; some known examples include disk type and aperture type. Some aperture type examples include "C" aperture, capital i or "I" aperture, hereinafter called an "H" aperture, triangle aperture, and bowtie aperture.

BRIEF DESCRIPTION OF THE DRAWINGS

FIG. 11 illustrates a spacing chart in one example of non-periodic spacing for different numbers of NFT's, in accordance with various aspects of the subject invention.

DETAILED DESCRIPTION OF THE INVENTION

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail to avoid unnecessarily obscuring the present invention.

Figure 1:
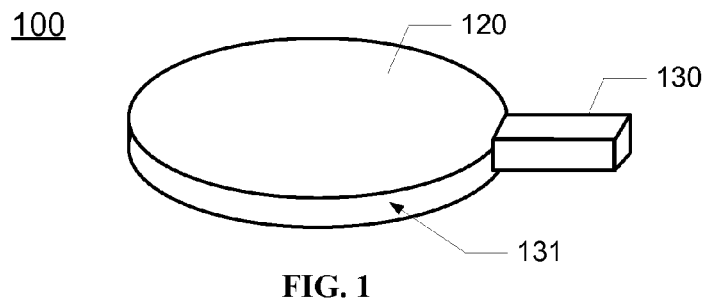
FIG. 1 illustrates a perspective view of a disk type NFT, in accordance with one aspect of the subject invention.

FIG. 1 is an illustration depicting a perspective view of a surface plasmon receptor disk type NFT 100 comprising a disk section 120 that has a side 131 and a pin section 130 connected to disk section 120.

Figure 2:
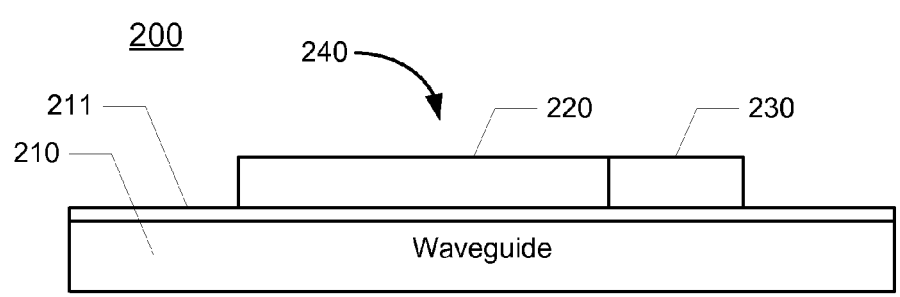
FIG. 2 illustrates a cross-sectional view of an NFT arrangement with waveguide, in accordance with one aspect of the subject invention.

FIG. 2 is a diagram depicting a cross-section view of an NFT arrangement 200 wherein a disk type NFT 240 comprises disk section 220 and pin section 230 coupled to a waveguide section 210. In one embodiment an optional intermediate layer 211 may be between the NFT 240 and waveguide section 210. In one embodiment, Intermediate layer 211 comprises alumina (Al2O3). In one embodiment, NFT 240 is located on and in contact with at least one surface of the waveguide 210. In one embodiment NFT 240 are on an intermediate layer 211 that is on and in contact with at least one surface of the waveguide 210. In one embodiment, intermediate layer 211 may comprise material that is substantially transparent to light. In one embodiment, the intermediate layer 211 may comprise a multilayer structure and may comprise different compositions. In a further embodiment, intermediate layer 211 may comprise layers having different indexes of refraction. In the illustrated example, the waveguide section 210 may be a waveguide core layer. In the foregoing descriptions, disk type NFT's are used for illustrative examples; however any type surface plasmon receptor or NFT may be used. Hereinafter, the term NFT is intended to include any type of surface plasmon receptor or NFT style.

Figure 3:
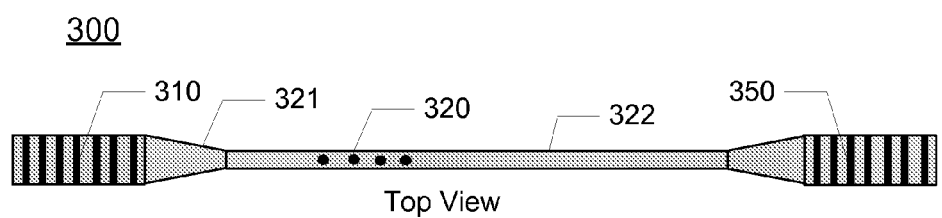
FIG. 3 illustrates a waveguide with multiple NFT's in a top view, in accordance with one aspect of the subject invention.

FIG. 3 illustrates one embodiment of test structure 300 with NFT's 320 in a top view. Test structure 300 has an input grating 310 and output grating 350. In one embodiment, the test structure 300 may comprise core material Ta2O5, although other materials may be used. In one embodiment, the input grating 310 and output grating 350 may be operated interchangeably. Test structure 300 may have light directing features, such as light funnel 321 to direct light into waveguide section 322. A plurality of NFT's is shown in FIG. 3, and different numbers may be used in some embodiments. The advantages of having multiple NFT's will be discussed in the following descriptions and figures.

Figure 4:
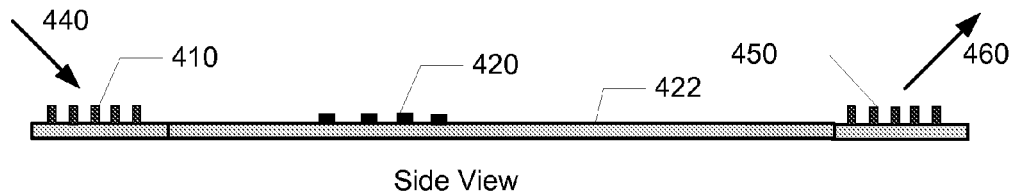
FIG. 4 illustrates a waveguide with multiple NFT's in a side view, in accordance with one aspect of the subject invention.

FIG. 4 illustrates a side view of test structure 300 shown in FIG. 3. Waveguide section 422 may be connected with input grating 410 for receiving input light 440, NFT's 420, and output grating 460 for emitting light 460. Gratings are shown highly simplified for illustration, and shown as raised features; however gratings may be constructed by various means including additive and subtractive processes.

Figure 5:
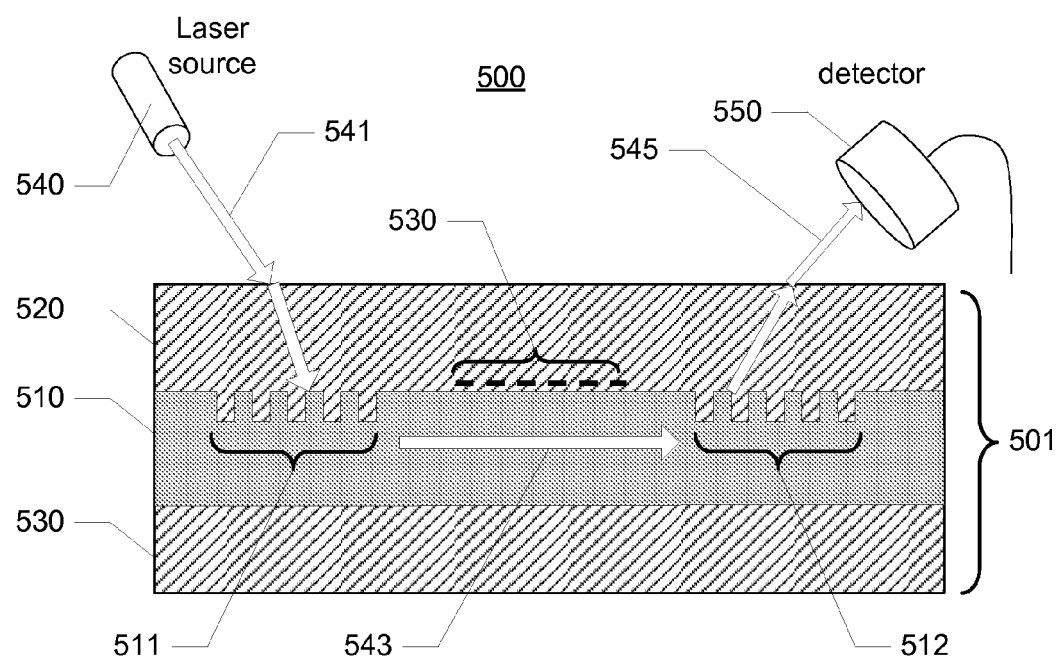
FIG. 5 illustrates a system for testing NFT's on a waveguide, in accordance with one aspect of the subject invention.

FIG. 5 illustrates one embodiment of a system 500 for testing the absorption of energy from a waveguide by NFT's. System 500 includes test structure 501 for testing the performance of NFT's 530. In one embodiment, test structure 501 may be installed on a wafer, and in another embodiment, test structure 501 may be installed in dicing lanes on a wafer. Test structure 501 comprises a core layer 510, bottom cladding layer 530, and top cladding layer 520. In one embodiment, cladding layers 520 and 530 comprise alumina; however, other materials can be used. Core layer 510 has an input grating 511 and output grating 512. In one embodiment, input grating 511 and output grating may 512 be used interchangeably. A light power source 540 applies a first light power 541 into test structure 501. Light power source 540 may be a laser diode. First light power 541 enters top cladding layer 520 and transmits through top cladding layer 520 into input grating 511. In one embodiment, light power 541 has a first wavelength and input grating 511 may be adapted to receive the first wavelength. Light power 541 inputted into input grating 511 transmits through core layer 510 via path 543, passing NFT's 530 toward output grating 512. Output grating 512 may be adapted to receive the light power and emit the light power out of output grating 512. The emitted light power propagates though top cladding layer 520 and exits as emitted light power 545. A photodetector 550 may be placed in path of the emitted light power 545 and may be adapted to measure the intensity of the light power emitted. NFT's 530 will absorb light power passing through the core layer 510, reducing the amount of light power available to output grating 512. In one embodiment, the loss of light received by the output grating may be used as a measure of the efficiency of the NFT's to absorb light power and thereby provide a measure of the performance of the NFT.

In one embodiment, the system 500 shown in FIG. 5 may be effective to measure the performance of the core layer 510 and NFT's 530; however, there still exists some uncertainty as to how much light energy is being transferred from the core layer 510 to the NFT's 530. There are energy losses throughout the system that reduce the amount of light energy exiting the output grating 512 besides the NFT's 530. For example, light power may be lost due to transfer efficiency of the top cladding 520, the input grating 511, the core layer 510, or the output grating 512. These and other losses make it difficult to precisely measure how much energy is actually transferred to the NFT's 530.

In order to overcome this uncertainty; some embodiments of the invention employ more than one test structure.

Figure 6:
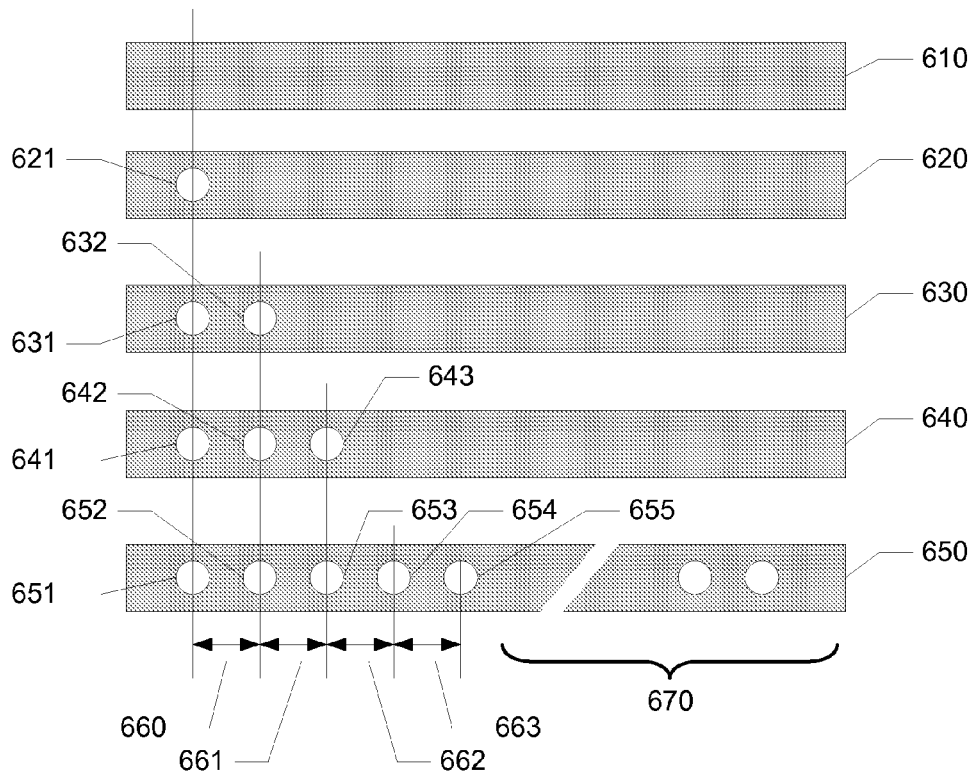
FIG. 6 illustrates embodiments of waveguides with different quantities of NFT's, in accordance with various aspects of the subject invention.

FIG. 6 illustrates test structure embodiments having waveguides with different numbers of NFT's. Different test structures can be used in combination to accurately measure the absorption of light energy by the NFT's. For clarity, input and output gratings and other features are not shown. First test structure 610 may be without any NFT's. First test structure 610 may be used as a baseline to determine the efficiency of the first test structure 610 without any NFT's absorption. Second test structure 620 includes one NFT 621. In one embodiment, a first light power may be input into the first test structure 610 and a first output light power measured at the output of test structure 610. Light power of the same first light power may be input into second test structure 620 and a second output light power may be measured at the output of test structure 620. Since the only difference between the first test structure 610 and the second test structure 620 is the addition of NFT 621, the difference in the measure of the first light power and the second light power represents the amount of light power absorbed by NFT 621.

The method described using first test structure 610 and second test structure 620 significantly improves the ability to measure the absorption of energy by the NFT 621; however, further improvements in accuracy can be obtained. If the absorption of the NFT 621 is small with respect to the other system losses or the precision of light measuring, it may be hard to accurately measure the performance of a single NFT.

Performance measuring of NFT's may be undertaken to optimize the NFT design. In one example, the NFT absorption may be measured over various wavelengths of light. This may assist in the design of the NFT, core layer, grating, cladding, or other aspects. However, with a single NFT, small changes may not be precisely measured.

Test structure 630 has NFT's 631-32 separated by spacing 660. Instead of using a single NFT and comparing to a baseline of no NFT, the absorption by NFT's 631-32 in test structure 630 is doubled, and measurement differences between test structure 610 and test structure 630 more easily measured. The absorption of one NFT 631 or NFT 632 in this example will be one half of the difference measured between output light powers of test structure 610 and test structure 630. This technique can be further improved by adding more NFT's. Test structure 640 has three NFT's 641-43 separated by spacing 660 and spacing 661. The method can be extended to any number of NFT's needed to cause absorption of the NFT's to be readily measured. Test structure 650 shows NFT's 651-55 and additional NFT's 670. The NFT's are separated by spacing 660-63. In one embodiment Spacing 660-63 may be the same, and in one embodiment, each of the spacing 660-63 may be selected to reduce interference.

In one embodiment, measurements are taken on two test structures that have a different number of NFT's. For example, output light power from test structure 620 with one NFT may be compared to output light power from test structure 640 with three NFT's, and the difference in output light power corresponds to the absorption by the different number of NFT's, in this case two. This can be extended to improve accuracy by using a greater number of NFT's on both test structures. For example, a first test structure may have ten NFT's and a second test structure may have twenty. In this case, the difference in output power is large, easily measurable, and dividing by ten yields the single NFT absorption.

Figure 7:
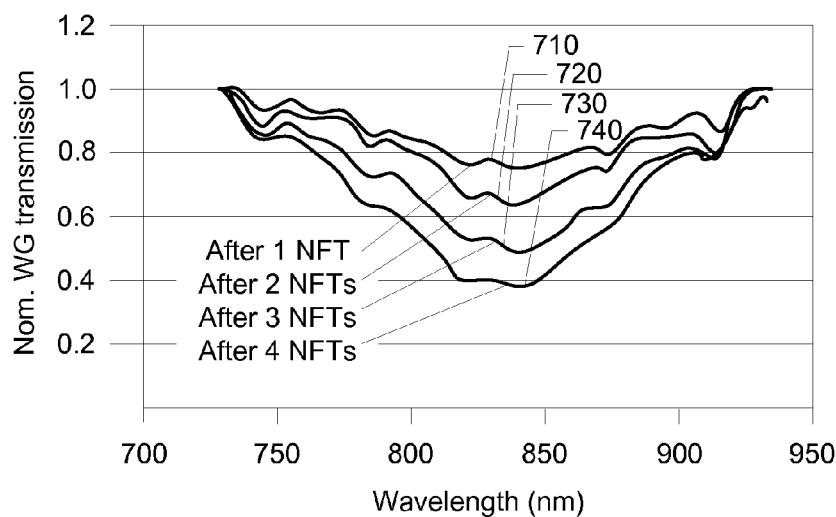
FIG. 7 illustrates an absorption chart for different numbers of NFT's on a waveguide, in accordance with various aspects of the subject invention.

FIG. 7 illustrates a chart showing NFT power absorption as a factor of input light wavelength. Curve 710 is a measure of light transmission through a test structure with one NFT as the input light wavelength varies. Curve 710 provides useful information, however, has a large factor of uncertainty due to a relatively flat and noisy response. It may be difficult to make an accurate assessment of the point of maximum absorption of the NFT in this example. Curve 720 shows a similar curve but with two NFT's on the test structure. The sensitivity to input wavelength may be significantly improved with two NFT's. Similarly, curve 730 shows the response with three NFT's and curve 740 shows the response with four NFT's. Curve 740 provides a much better measure of the sensitivity of the NFT's to changes in input wavelength. The data from any two curves may be used to obtain the absorption of NFT's as previously described.

In the preceding example, the variable under test was sensitivity of the NFT to the input light wavelength. Other variables may be similarly measured, such as core material, intermediate layer thickness, cladding, NFT size or shape, or other parameters.

Figure 8:
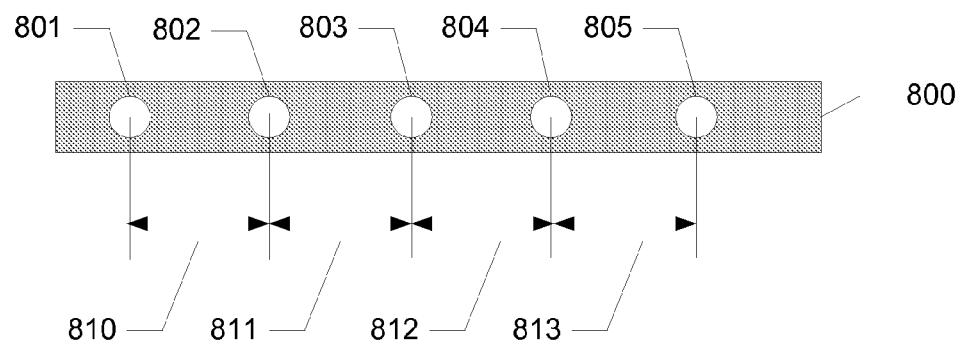
FIG. 8 illustrates NFT's with periodic spacing on a waveguide, in accordance with one aspect of the subject invention.

FIG. 8 illustrates one embodiment of a test structure 800 with NFT's 801-805. For clarity, input grating, output grating, and other structures are not shown. First spacing 810 measures center-to-center distance between NFT 801 and NFT 802. In one embodiment, first spacing 810 may be greater than one micron. In one embodiment, first spacing 810 may be approximately 4 microns. In one embodiment, first spacing may be between 3 and 10 microns. First spacing 810 may be selected by other criteria, for example, in relation to the wavelength of light being used. In test structure 800, spacing 810, 811, 812, and 813 are substantially equal. In some embodiments, spacing 810, 811, 812, and 813 are not substantially equal. These alternative selections may be advantageous to provide or avoid constructive or destructive interference, and will be discussed in the following descriptions.

Figure 9:
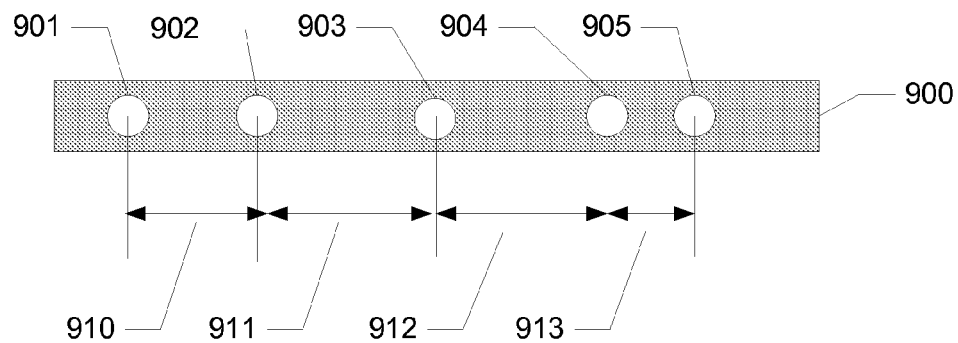
FIG. 9 illustrates NFT's with non-periodic spacing on a waveguide, in accordance with one aspect of the subject invention.

FIG. 9 illustrates one embodiment of a test structure 900 with NFT's 901-905. For clarity, input grating, output grating, and other structures are not shown. First spacing 910 measures center-to-center distance between NFT 901 and NFT 902. In one embodiment, first spacing 910 may be approximately 4 microns; however, spacing may be selected by other criteria, for example, in relation to the wavelength of light being used. Spacing 911 measures the center-to-center spacing between NFT 902 and NFT 903. Similarly, spacing 912 measures the spacing between NFT 903 and NFT 904, and spacing 913 measures the spacing between NFT 904 and NFT 905. In one embodiment, spacing 910-13 are selected to avoid wave interference or back reflections. By intentionally avoiding interference caused by reflections from other NFT's on the waveguide 900, an improved measurement may be obtained.

Figure 10:
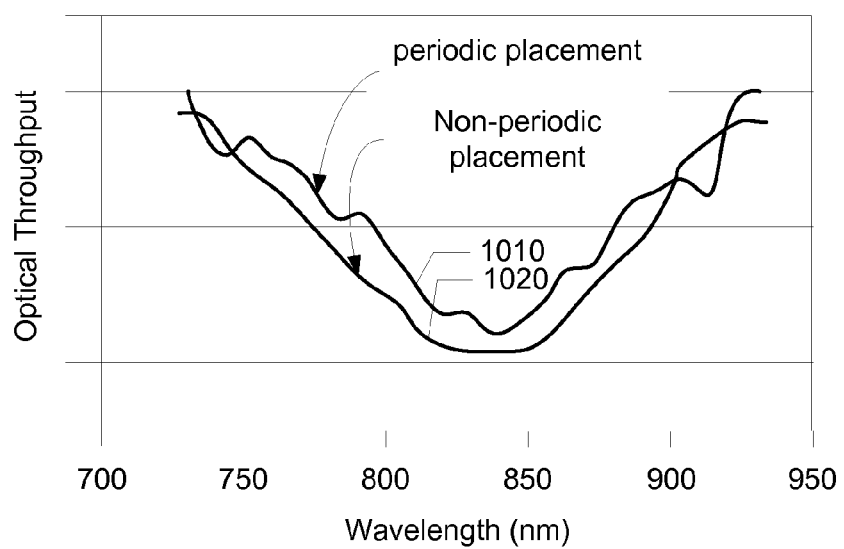
FIG. 10 illustrates optical throughput measurements with periodic and non-periodic spacing, in accordance with various aspects of the subject invention.

FIG. 10 illustrates one example of optical performance that results from periodic and non-periodic NFT spacing. Curve 1010 shows an example of optical throughput obtained from NFT's with periodic spacing. Curve 1010 has irregular shape due to the constructive and destructive interference caused by reflections from NFT's on the waveguide. This interference affects the data readings and results in reduced accuracy of measurement of the NFT performance. Curve 1020 shows an example of the same NFT's, however spaced non-periodically. It can be seen that the curve is relatively free from the interference caused by reflections, and results in improved measurement accuracy of NFT performance.

Non-periodic spacing can be selected to reduce interference of a plurality of NFT's on a test structure. In one embodiment, selection of spacing may be based on the wavelength of input light and the refractive index of the waveguide. In one embodiment, the center-to-center spacing ($d_m$) of a plurality of surface plasmon receptors may be selected according to the formula:

$$d_m = d_0 + \frac{\lambda}{2n} \times \frac{(m-1)}{(N-1)},$$

where
$d_o$ is a value greater than one micron (μm);
$\lambda$ A is the wavelength of light coupled into the waveguide;
n is effective refractive index of the waveguide;
N is the total number of the NFT's, and
m is a sequential number of the plurality of the surface plasmon receptors.

FIG. 11 is a table showing one example of center-to-center spacing for test structures having between two and eight NFT's. In this example, $d_o$ is selected to be 4 μm, λ is selected to be 0.83 μm, and n is selected to be 1.8.

For example, the table column labeled N=4 is a test structure with 4 NFT's. The spacing between the first NFT and the second NFT (m=1) is the selected value 4 μm, the spacing between the second and third NFT (m=2) is 4.077 μm, and the spacing between the third NFT and fourth NFT (m=3) is 4.154 μm. Other entries are interpreted in a similar manner.

Figure 12:
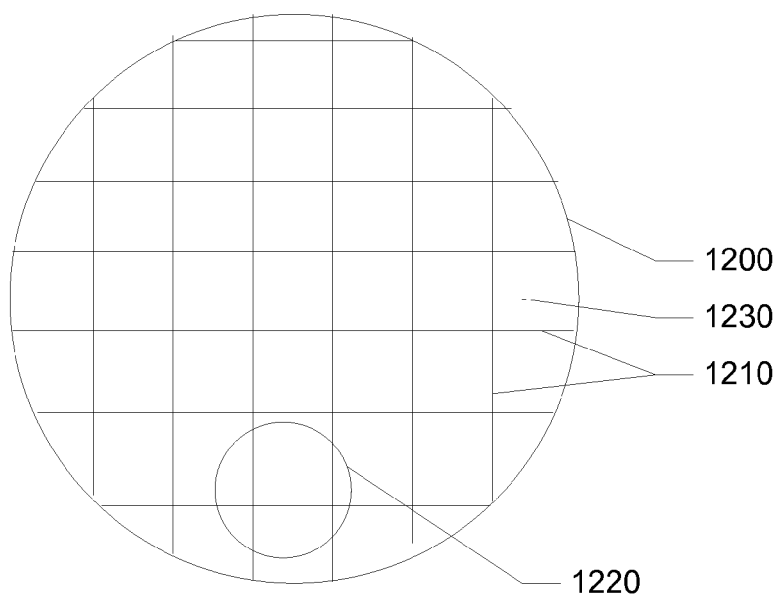
FIGS. 12 and 12a illustrate a wafer with dicing lanes and test structures, in accordance with one aspect of the subject invention.
Figure 12A:
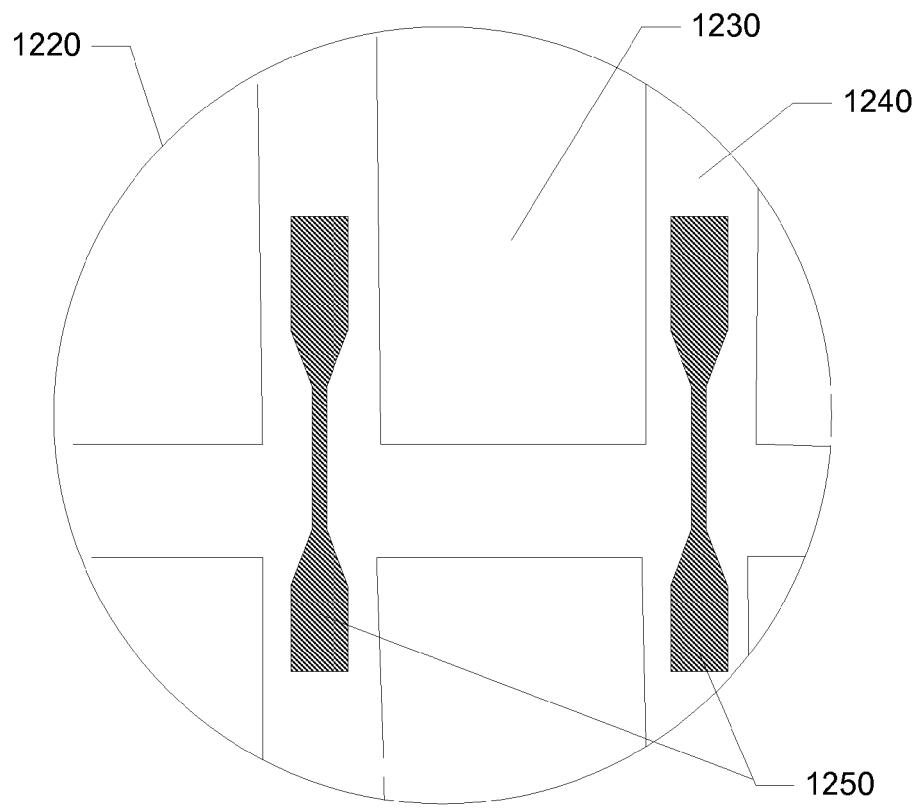

FIGS. 12 and 12a illustrate a highly simplified view of a wafer 1200 and enlarged section 1220 of one embodiment that incorporates test structures. Wafer 1200 may have many devices in area 1230 that incorporate waveguides and NFT's. These devices may be separated by dicing channels 1210 to facilitate separating the devices (sawing or dicing) from the wafer. FIG. 12a is an enlarged view of area 1220 and illustrates test structures 1250 positioned in the dicing channels 1240. This is a common technique for placing test structures on wafers so that valuable wafer space can be conserved for devices, since the test structures are only using space that will be sawn away at a later step of fabrication. In other embodiments, the test structures may be placed at any location. The test structures 1250 may be formed at the same time as the waveguides, NFT's, or other structures in area 1230 are formed. The waveguides and NFT's on the test structures can be tested after this stage of fabrication, and any anomalies discovered early in the process.

Figure 13:
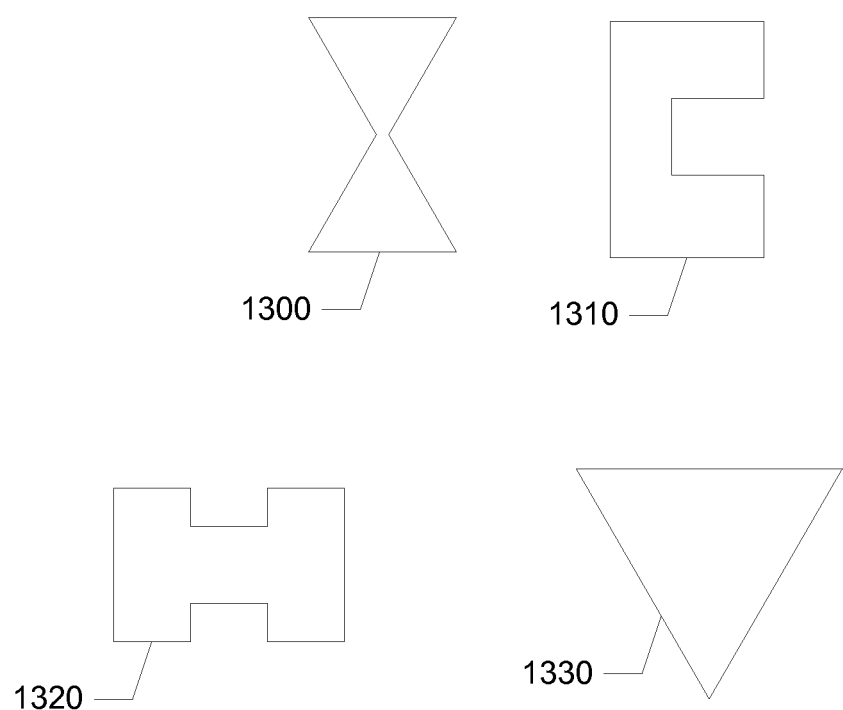
FIG. 13 illustrates several NFT types, in accordance with various aspects of the subject invention.

FIG. 13 illustrates several NFT types, including bowtie NFT 1300, "C" shape NFT 1310, "H" shape NFT 1320, and triangle NFT 1340. These and any other NFT shapes or surface plasmon receptors may be used in embodiments of the test structures described in the preceding sections.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

We claim:
1. A structure for measuring energy absorption by a surface plasmon receptor on a waveguide comprising:
    a first waveguide;
    a first input grating for coupling light comprising a first wavelength into the first waveguide;
    a first output grating for coupling light out of the first waveguide;
    a first plurality of surface plasmon receptors in cooperation with the first waveguide to receive light energy and located between the first input grating and the first output grating, and
    wherein the first plurality of surface plasmon receptors have substantially equal center to center spacing ($d_c$) between adjacent surface plasmon receptors; wherein the $d_c$ is between 3 µm and 10 µm.
2. The structure of claim 1 wherein the first plurality surface plasmon receptors are on and in contact with at least one surface of the waveguide.
3. The structure of claim 1 wherein the first plurality surface plasmon receptors are on an intermediate layer that is on and in contact with at least one surface of the waveguide.
4. The structure of claim 3 wherein the intermediate layer comprises a material substantially transparent to light of the first wavelength.
5. The structure of claim 1 wherein the first plurality of surface plasmon receptors comprise a near field transducer (NFT).
6. The structure of claim 5 wherein the NFT comprises a flat surface comprising a disk shape and an outer side edge.
7. The structure of claim 6 further comprising a pin attached to the outer side edge.
8. The structure of claim 5 wherein the NFT comprises at least one of:
    a "C" shape;
    an "H" shape;
    a bowtie shape, and
    a triangle shape.
9. The structure of claim 1 further comprising:
    a second waveguide;
    a second input grating for coupling light into the second waveguide;
    a second output grating for coupling light out of the second waveguide;
    a second plurality of surface plasmon receptors between the second input grating and the second output grating and in cooperation with the second waveguide to receive light energy, wherein:
    the second plurality is less than or greater than the first plurality.
10. The structure of claim 1 wherein the first plurality of surface plasmon receptors are spaced comprising a spacing that is not substantially equal and selected to reduce back reflection interference between surface plasmon receptors.
11. The structure of claim 10 wherein a center to center spacing ($d_m$) of the first plurality of surface plasmon receptors is selected according to the formula:

$$d_m = d_0 + \frac{\lambda}{2n} \times \frac{(m-1)}{(N-1)},$$

where
    $d_o$ is a value greater than one micron (µm);
    $\lambda$ is the first wavelength of light coupled into the first waveguide;
    n is effective refractive index of the first waveguide;
    N is the total number of the surface plasmon receptors, and
    m is a sequential number of the plurality of the surface plasmon receptors.
12. A method for measuring surface plasmon absorption of energy on a waveguide comprising:
    providing a first waveguide comprising a first input grating for coupling light into the first waveguide and a first output grating for coupling light out of the first waveguide;
    providing a second waveguide comprising a second input grating for coupling light into the second waveguide and a second output grating for coupling light out of the second waveguide;
    providing a first plurality of surface plasmon receptors on the first waveguide between the first input grating and the first output grating;
    providing a sensor to measure light power from the first output grating and the second output grating;
    inputting an input light power comprising a first wavelength into the first waveguide first input grating and measuring a first output light power from the first waveguide first output grating;
    inputting the input light power at the first wavelength into the second waveguide second input grating and measuring a second output light power from the second waveguide second output grating;
    taking a difference between the first output light power and the second output light power as a first measurement of the absorption of the surface plasmon receptors on the first waveguide at the first wavelength;
    inputting the input light power comprising:
    a second wavelength into the first waveguide first input grating and measuring a third output light power from the first waveguide first output grating;
    inputting the input light power at the second wavelength into the second waveguide second input grating and measuring a fourth output light power from the second waveguide second output grating;
    taking a difference between the third output light power and the fourth output light power as a second measurement of the absorption of the surface plasmon receptors on the first waveguide at the second wavelength, and
    taking a difference in the first measurement and the second measurement as a measure of absorption of the surface plasmon receptors variance as a function of input light power wavelength.
13. A method for measuring surface plasmon absorption of energy on a waveguide comprising:
    providing a first waveguide comprising a first input grating for coupling light into the first waveguide and a first output grating for coupling light out of the first waveguide;
    providing a first plurality (N1) of surface plasmon receptors on the first waveguide between the first input grating and the first output grating;
    providing a second waveguide comprising a second input grating for coupling light into the second waveguide and a second output grating for coupling light out of the second waveguide;
    providing a second plurality of surface plasmon receptors on the second waveguide between the second input grating and the second output grating, wherein the second plurality (N2) of surface plasmon receptors is greater than the first plurality (N1) of surface plasmon receptors;

providing a sensor to measure light power from the first output grating and the second output grating;

inputting an input light power comprising a first wavelength into the first waveguide first input grating and measuring a first output light power from the first output grating of the first waveguide;

inputting the input light power comprising the first wavelength into the second waveguide second input grating and measuring a second output light power from the second output grating of the second waveguide, and taking a difference between the first output light power and the second output light power as a measurement of the absorption of N2 minus N1 surface plasmon receptors at the first wavelength.

14. The method of claim 13 further comprising inputting the input light power comprising a second wavelength into the first waveguide first input grating and measuring a third output light power from the first waveguide first output grating;

inputting the input light power at the second wavelength into the second waveguide second input grating and measuring a fourth output light power from the second waveguide second output grating;

taking a difference between the third output light power and the fourth output light power as a second measurement of the absorption of the surface plasmon receptors on the first waveguide at the second wavelength, and taking a difference in the first measurement and the second measurement as a measure of absorption of the surface plasmon receptors variance as a function of input light power wavelength.

* * * * *